United States Patent [19]

Ley et al.

[11] Patent Number: 4,495,366

[45] Date of Patent: Jan. 22, 1985

[54] PROCESS FOR MAKING TRIFUNCTIONAL PRIMARY AMINE CROSSLINKER

[75] Inventors: David A. Ley, Stamford, Conn.; Herbert Burkhard, Eastchester, N.Y.

[73] Assignee: American Cyanamid Company, Stamford, Conn.

[21] Appl. No.: 529,233

[22] Filed: Sep. 6, 1983

[51] Int. Cl.³ .................................................. C07C 102/06
[52] U.S. Cl. ......................................................... 564/160
[58] Field of Search ............................................ 564/160

[56] References Cited

U.S. PATENT DOCUMENTS

| | | | |
|---|---|---|---|
| 2,820,021 | 1/1958 | Franko-Filipasic | 564/160 X |
| 3,048,620 | 8/1962 | Spivack | 564/160 X |
| 3,159,538 | 12/1964 | Nordmann | 564/160 X |
| 3,933,663 | 1/1976 | Thompson et al. | 564/160 X |
| 3,953,396 | 4/1976 | Thompson | 564/160 X |
| 4,143,070 | 3/1979 | Walker | 564/160 X |
| 4,278,814 | 7/1981 | Sachdev | 564/160 |

*Primary Examiner*—Paul F. Shaver
*Attorney, Agent, or Firm*—Steven J. Hultquist

[57] ABSTRACT

An improved process for synthesizing a sterically unhindered trifunctional primary amine is provided. This process includes the steps of slowly adding a particular unsaturated diester to a solution of a certain diamine in an aromatic organic solvent, and recovering the desired compound. The trifunctional primary amine is useful as a crosslinking agent.

9 Claims, No Drawings

PROCESS FOR MAKING TRIFUNCTIONAL PRIMARY AMINE CROSSLINKER

TECHNICAL FIELD

This invention relates to a polyamine crosslinking agent. More particularly, this invention relates to an improved process for making a certain polyamine crosslinking agent.

BACKGROUND ART

The reaction of maleic diesters with certain diamines is known, as illustrated by the work of Yu. T. Tanchuk and I. A. Ral'chuk, J. Organic Chem. U.S.S.R., Vol. 14, pp. 2083–2088 (1978). In this work, the reported reaction products are a polyamide that retains the maleic acid double bond, an addition product in which each amine group of the diamine has added by Michael reaction to the double bond of a maleic diester, and a maleic diester derivative in which one of the ester groups has been replaced by an amide group (an amic ester).

Furthermore, we are aware of a prior invention disclosed and claimed in copending application U.S. Ser. No. 529,234, filed Sept. 6, 1983 in the name of Roland DiLeone, and directed to a trifunctional primary amine crosslinking agent and to a process for synthesizing the crosslinking agent. This prior proccess includes the steps of heating a reaction vessel containing an unsaturated diester of the formula

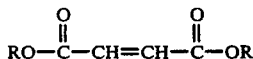

in which R is an alkyl of 1–4 carbon atoms, and a diamine of the formula

in which n=4–8, so as to remove by distillation, the alcohol reaction byproduct, and then recovering a trifunctional primary amine crosslinking agent of the formula

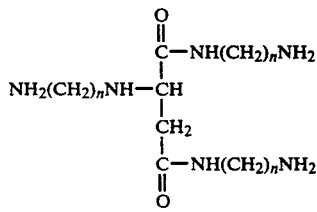

in which n=4–8. The diamine/diester molar ratio is at least about 3:1. A problem with this process is the variability in yield of the desired trifunctional primary amine product of the process. In view of the usefulness this amine was found to have as a crosslinking agent for compositions based upon amine-reactive polymers, there has existed a continuing need for an improved process of making the trifunctional primary amine. Hence, the provision of such an improved process would constitute a significant advance in the art.

SUMMARY OF THE INVENTION

It is accordingly one object of the present invention to provide an improved process for forming the trifunctional primary amine crosslinking agent of the formula set forth above.

Additional objects, advantages and novel features of the invention will be set forth in the description which follows, and in part will become apparent to those skilled in the art upon examination of the following or may be learned by practice of the invention.

To achieve the foregoing object and in accordance with the purpose of the present invention, as embodied and broadly described herein, there is provided an improved process for synthesizing the trifunctional primary amine crosslinking agent described above. This process includes the steps of slowly adding an unsaturated diester of the formula

in which R is an alkyl of 1–4 carbon atoms, to a solution of a diamine of the formula

in which n=4–8, and then recovering the desired compound. The diamine is dissolved in an aromatic organic solvent, the diamine solution is under reflux conditions during the addition, and the diamine/diester molar ratio is at least about 3:1.

This process has the advantage of reliably making the trifunctional primary amine in consistent good product yields.

DETAILED DESCRIPTION OF THE INVENTION

As explained, the present invention is directed to an improved process of making a trifunctional primary amine of the formula

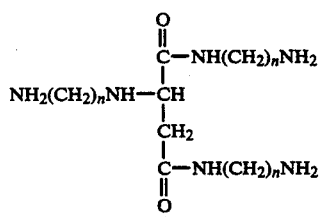

in which n=4–8. In a preferred embodiment of the trifunctional primary amine, n=6, and the compound has the name N,N'-bis(6-aminohexyl)-2-[(6-aminohexyl)amino] butanediamide. This process uses as reactants an unsaturated diester of the formula

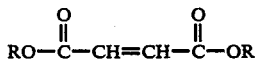

in which R is an alkyl of 1–4 carbon atoms, and a diamine of the formula

in which n=4–8. The diester is an ester of either maleic or fumaric acid, with a convenient diester being dimethyl maleate. Another particularly suitable diester is diethyl maleate. The preferred amine is 1,6-hexanediamine.

An essential feature of the process of the present invention is that the diamine/diester molar ratio be at least about 3:1, with about 3:1 being convenient. If a molar ratio of more than about 3:1 is used, typically the molar ratio will be only slightly more than 3:1, with about 5:1 being a practical upper limit because of difficulty in removing the unreacted excess of diamine.

We have surprisingly discovered that synthesis of the trifunctional primary amine in good yields is facilitated when the diester is slowly added to a solution of the diamine in an aromatic organic solvent. As used herein, the term "slowly added" is intended to be broadly construed to encompass any non-bulk addition of diester to the diamine solution, wherein the diester is added in sequential portions to the diamine solution and each added portion is substantially reacted prior to addition of the next portion to the solution. As hereinafter described, a preferred mode of introducing the diester to the diamine solution is by dropwise addition. We carry out the addition with the contents of the reaction vessel under reflux conditions. We have found that mild reflux is convenient, and we effect the slow addition by using dropwise addition of the diester to the diamine. As can be understood by one skilled in the art, the time required to complete the addition depends upon, for example, the total volume of the diester being added. The solvent can be any aromatic organic solvent. Exemplary solvents include benzene, toluene and xylene. Conveniently, the reaction is carried out under ambient atmosphere.

During the time that the addition is being carried out, the reaction temperature rises as a result of an increased boiling point of the reaction vessel contents. Preferably, in order to push the reaction to completion, the alcohol byproduct is removed by distillation, after the addition is finished. In this case, an aromatic solvent is preferably added to maintain or approximately maintain reaction volume. The reaction may be followed by amine titration or by disappearance of the ester in the $^1$H NMR spectrum. After the reaction is complete, the desired trifunctional primary amine is conveniently recovered by removing the aromatic solvent.

This trifunctional primary amine is useful as a crosslinking agent for compositions based upon an amine-reactive polymer, such as in epoxy systems. These compositions are useful for coatings and adhesive applications. Conveniently, the amine-reactive polymer contains repeating units derived from an activated ester-containing vinyl monomer of the formula

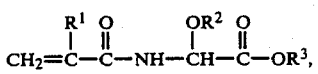

in which the $R^1$ group is selected from H and Me, the $R^2$ group is selected from alkyls of 1-6 carbon atoms, cycloalkyls of 5-6 carbon atoms, and 2-hydroxyalkyls of 2-6 carbon atoms, and the $R^3$ group is selected from alkyls of 1-6 carbon atoms, cycloalkyls of 5-6 carbon atoms, and 2-hydroxyalkyls of 2-6 carbon atoms. Polymers of this type are described in U.S. Pat. application Ser. No. 346,329, filed Feb. 5, 1982, the relevant portions of the description of which are hereby incorporated by reference into this description. An advantage of this crosslinking agent is that it makes possible low temperature cure.

In the Examples which follow, all parts and percentages are by weight unless otherwise specified.

EXAMPLE 1

Dimethyl maleate (72 g, 0.5 moles) is added over a 2-3 hour period to a solution of 1,6-hexanediamine (174 g, 1.5 moles) in toluene (360 g) at 75°–80° C. The reaction temperature rises from 80° to 110° C. under reflux conditions. After the addition is completed, methanol is distilled at a reaction temperature of 120°–125° C. Additional toluene (320 g) is added to maintain reaction volume. The reaction may be followed by amine titration or by disappearance of the methyl ester in the $^1$H NMR spectrum. After the reaction is complete, toluene is removed under vacuum (50°–70° C., 15–20 mm Hg) to give a viscous liquid which solidifies on standing. Potentiometric analysis indicates a 3/1 ratio of primary to secondary amine. NMR and IR spectra are consistent with the desired N,N'-bis(6-aminohexyl)2-[(6-aminohexyl)amino] butanediamide structure.

EXAMPLE 2

The procedure of Example 1 is repeated except hat diethyl maleate (86 g, 0.5 moles) is substituted for the dimethyl maleate, and the reaction temperature is 125°–150° C. rather than 120°–125° C.

The above examples are illustrative of this invention. It is to be understood that the examples are not in any way to be interpreted as limiting the scope of the invention. Rather, it is intended that the scope of the invention be defined by the claims set forth below.

We claim:

1. An improved process of making a trifunctional primary amine compound of the formula

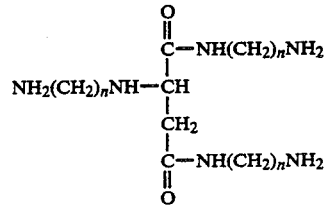

wherein n=4-8; said process comprising (a) slowly adding an unsaturated diester of the formula

wherein R is an alkyl of 1-4 carbon atoms, to a solution of a diamine in an aromatic organic solvent, the solution being under reflux conditions and the diamine/diester molar ratio being at least about 3:1; wherein the diamine is of the formula

wherein n is the same as above; and (b) recovering said trifunctional primary amine compound.

2. The process of claim 1, wherein the diester is dimethyl maleate.

3. The process of claim 1, wherein the diester is diethyl maleate.

4. The process of claim 1, wherein the diamine is 1,6-hexanediamine.

5. The process of claim 1, wherein n=6 in said trifunctional primary amine compound.

6. The process of claim 1, wherein the diamine/diester molar ratio is about 3:1.

7. The process of claim 1, wherein the aromatic solvent is toluene.

8. The process of claim 1, further comprising the step of removing the alcohol byproduct by distillation after the addition is finished.

9. Tlhe process of claim 8, further comprising the step of adding aromatic solvent to substantially maintain reaction volume after the alcohol byproduct removal step.

* * * * *